United States Patent [19]

Schilling, Jr. et al.

[11] 4,414,403

[45] Nov. 8, 1983

[54] BRANCHED POLYCARBOSILANES AND THEIR USE IN THE PRODUCTION OF SILICON CARBIDE

[75] Inventors: Curtis L. Schilling, Jr., Croton-On-Hudson, N.Y.; Thomas C. Williams, Ridgefield, Conn.; John P. Wesson, Croton-On-Hudson, N.Y.

[73] Assignee: Union Carbide Corporation, Danbury, Conn.

[21] Appl. No.: 361,106

[22] Filed: Mar. 23, 1982

Related U.S. Application Data

[63] Continuation-in-part of Ser. No. 272,900, Jun. 18, 1981, abandoned, which is a continuation-in-part of Ser. No. 209,151, Nov. 21, 1980, abandoned.

[51] Int. Cl.$^3$ ................................................ C07F 7/08
[52] U.S. Cl. .................................... 556/430; 556/435; 106/44; 423/345; 501/88
[58] Field of Search ................................. 556/430, 435

[56] References Cited

U.S. PATENT DOCUMENTS

| | | | |
|---|---|---|---|
| 2,352,974 | 7/1946 | Rochow | 556/435 X |
| 2,483,972 | 10/1949 | Goodwin | 260/448.2 |
| 2,697,029 | 12/1954 | Baker et al. | 23/209.1 |
| 2,850,514 | 9/1958 | Knoth | 260/448.2 |
| 3,050,366 | 8/1962 | Ringwald | 556/435 X |
| 3,422,039 | 1/1969 | Nametkin et al. | 556/435 X |
| 3,580,940 | 5/1971 | Webster | 556/435 |
| 4,052,430 | 10/1977 | Yajima et al. | 260/448.2 D |
| 4,100,233 | 7/1978 | Yajima et al. | 423/345 |
| 4,105,455 | 8/1978 | Koga et al. | 106/44 |

FOREIGN PATENT DOCUMENTS

| | | | |
|---|---|---|---|
| 498984 | 1/1954 | Canada | 556/430 |
| 54-65799 | 5/1979 | Japan . | |
| 143803 | 4/1961 | U.S.S.R. | 556/430 |

OTHER PUBLICATIONS

Nefedov et al., Proc. Acad. Set., USSR, 76-8 154, 76-8, (1964).
"J. Organometal. Chem.", 6, pp. 665-668, 1966.
"J. Organometal Chem.", 5, pp. 199-200, 1966.
"J.A.C.S.", 86, No. 7, p. 1454, 4/5/64.

Primary Examiner—Paul F. Shaver
Attorney, Agent, or Firm—Eugene C. Trautlein

[57] ABSTRACT

Silicon carbide can be produced by the pyrolysis of branched polycarbosilanes which in turn are produced directly from selected monomer systems.

20 Claims, No Drawings

BRANCHED POLYCARBOSILANES AND THEIR USE IN THE PRODUCTION OF SILICON CARBIDE

The U.S. Government has rights in this invention pursuant to Contract No. N00014-75-C-1024 awarded by the Office of Naval Research, Department of the Navy.

CROSS-REFERENCE TO RELATED APPLICATION

This is a continuation-in-part of U.S. patent application Ser. No. 272,900 which was filed on June 18, 1981 which is a continuation-in-part of U.S. patent application Ser. No. 209,151, which was filed on Nov. 21, 1980, both now abandoned.

FIELD OF THE INVENTION

This application relates to novel branched polycarbosilane compositions, to their production from selected monomer systems, and to their use in the production of silicon carbide.

DESCRIPTION OF THE PRIOR ART

Silicon carbide has long been known and appreciated for its chemical inertness, high temperature stability, semi-conductor properties, and especially its extreme hardness. The hardness of silicon carbide approaches that of diamond and boron nitride.

Silicon carbide was originally prepared by reacting inorganic materials, for example silica and a carbon source such as coke or graphite, at extremely high temperatures. More recently, various methods for preparing silicon carbide from organic materials such as silanes and other organic silicon derivatives have been discovered.

One widely reported approach is described in the following references: U.S. Pat. Nos. 4,052,430, 4,100,233, 4,105,455, 4,110,386, 4,117,057, 4,122,139, 4,134,759, 4,147,538, 4,159,259, Japanese Patent Disclosure No. 1979-65,799, Nakamura et al., *Chemical Abstracts*, 91:215596p, and Yajima et al., *Chemistry Letters*, 5, 435-6 (1976). That approach provides polycarbosilanes, some of which are soluble and thermoformable by standard methods, which can be pyrolized to silicon carbide. These polycarbosilanes are prepared by a pre-pyrolysis/rearrangement/polymerization of cyclic or linear polydimethylsilanes, which in turn are typically prepared from $(CH_3)_2SiCl_2$ and active metals.

More specifically, such prior art requires an active metal condensation of $Me_2SiCl_2$ to polydimethylsilanes (cyclic or linear), which are isolated and converted by application of heat (and pressure in the case of cyclics) to polycarbosilanes in a separate step, as illustrated by the equations:

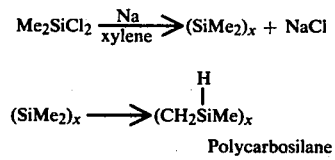

The crude polycarbosilanes so produced are often subjected to further treatments such as vacuum distillation and fractionation by precipitation from a nonsolvent to isolate polycarbosilanes of particular use in making silicon carbide fibers.

Such prior art contains some disclosures relating to starting materials other than $(CH_3)_2SiCl_2$. For instance, Japanese Patent Disclosure No. 1979-65,799 contains an Example 11 in which $(CH_3)_2SiCl_2$ and $CH_2=CH(CH_3)SiCl_2$ are reacted under conditions similar to those contemplated herein. However, since they are reacted in a molar ratio of more than 19:1, no appreciable amount of silicon carbide is obtainable from the reaction product; see Example F hereinbelow.

Another approach is described in U.S. Pat. No. 2,697,029 wherein carbonized substances containing silicon are obtained by pyrolysis of polymers prepared by addition polymerization of unsaturated organosilanes. This reference also discloses a molar functionality concept based solely upon the functionality derived from unsaturation, i.e., carbon double and triple bonds.

SUMMARY OF THE INVENTION

It has now been found that novel branched polycarbosilanes which can be pyrolized to silicon carbide can be prepared in one step from simple silane monomers or mixtures thereof containing vinyl halo or halomethyl moieties. More particularly, this invention comprises a process for the production of silicon carbide which comprises, first, reacting at least one silane capable of providing backbone branching at silicon with other silanes, such compound or mixture of compounds being selected such that the average molar functionality (as described hereinbelow) of the compound system to be reacted is at least 2.3 with an active metal or alloy thereof in an inert solvent at an elevated temperature to form a branched polycarbosilane composition, and, subsequently, pyrolizing the branched polycarbosilane composition in an inert atmosphere to form silicon carbide. The novel branched polycarbosilanes themselves constitute a key part of this invention.

DESCRIPTION OF THE PREFERRED EMBODIMENTS

In a broad aspect, this invention contemplates a process for the production of novel branched polycarbosilane compositions which comprises reacting, with an active metal or metal alloy in an inert solvent at an elevated temperature, a compound system comprising one or more monomers of formula I.

$$(CH_2=CH)_a R_b SiX_c (CH_2X)_d \quad (I)$$

wherein R is lower alkyl (e.g., of up to eight carbon atoms, and is preferably methyl), X is halo (preferably chloro), a is 0 or 1, b is 0-3, c is 0-4, d is 0-4, a+b+c+d totals 4, and a+c+d totals at least 3, or organodisilanes of formula (II).

$$R_e X_f Si(CH_2)_g SiX_h R_i \quad (II)$$

wherein R and X have the same significance as previously set forth, and the value of e, f, g, h and i are individually 0-3 such that f+h equals at least 3, such compound system being selected such that a plurality of the silyl units are at least trifunctional, i.e., are branching sites in the resultant polymer backbone and such that the formation of silane-carbon bonds is favored.

The monomer compound system of the present invention preferably contains silane mixtures of formula (I), at least one of which is characterized by an a+c+d total of 3 or 4, or a mixture of silanes of formula (I) and disilanes of formula (II) in order to permit selection of reactants such that the silyl units in the resultant polymer provide branching sites in the polymer.

Such branched polycarbosilanes may be described as compositions which comprise units derived from silanes of formula (I) as shown:

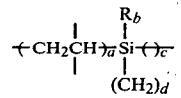

wherein R is lower alkyl (preferably methyl), a is 0 or 1, b is 0–3, c is 0–4, d is 0–4, and a+b+c+d totals 4, with the three essential provisos that, in each of the plural units a, b, c, d, and R may differ (depending on the monomer from which they originate), in at least one unit, a+d must total at least 1 (in order to provide Si-C bonds), and, in a plurality of the silyl units (which may but need not be the unit in which a+d totals at least 1), a+c+d totals at least 3.

Units derived from silanes of formula (II) may also be contained in branched polycarbosilane compositions as shown:

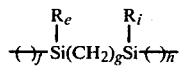

wherein r is lower alkyl (preferably methyl) e, f, g, h, and i are individually 0–3 and f+h equals at least 3.

A further aspect of the invention consists in pyrolyzing, by means in themselves known to those skilled in the art, the novel branched polycarbosilane compositions of the present invention in order to provide silicon carbide and products containing silicon carbide.

The following formulas (wherein R and X have the meanings indicated above) illustrate classes of compounds which can be utilized in the formation of the novel branched polycarbosilanes of the present invention:

| | |
|---|---|
| $CH_2=CHSiX_2(CH_2X)$ | $CH_2=CHSiX_3$ |
| $CH_2=CHR_2Si(CH_2X)$ | $R_3Si(CH_2X)$ |
| $CH_2=CHRSiX(CH_2X)$ | $R_2Si(CH_2X)_2$ |
| $SiX_4$ | $RSi(CH_2X)_3$ |
| $R_3SiX$ | $RSiX(CH_2X)_2$ |
| $CH_2=CHR_3Si$ | $RSiX_2(CH_2X)$ |
| $SiX(CH_2X)_3$ | $CH_2=CHRSiX_2$ |
| $SiX_2(CH_2X)_2$ | $CH_2=CHR_2SiX$ |
| $R_2SiX(CH_2X)$ | $RSiX_3$ |
| $R_2SiX_2$ | $SiX_3(CH_2X)$ |
| $R_3SiSiX_3$ | $R_3SiCH_2SiX_3$ |
| $XR_2SiSiR_2X$ | $XR_2SiCH_2CH_2SiR_2X$ |
| $X_2RSiSiR_2X$ | $X_2RSiCH_2CH_2SiR_2X$ |
| $X_2RSiSiRX_2$ | $X_2RSiCH_2CH_2SiRX_2$ |

As indicated, it is preferred to use a mixture (i.e. two or more silane compounds selected from different classes) to make the novel branched polycarbosilanes. Such mixtures include, but are not limited to:
$CH_2=CHRSiX_2/R_2SiX(CH_2X)$
$CH_2=CHRSiX_2/R_3SiX$
$R_2SiX(CH_2X)/RSiX_3$
$CH_2=CHRSiX_2/CH_2=CHR_2SiX/R_3SiX$
$CH_2=CHRSiX_2/R_2SiX(CH_2X)/R_3SiX$
$CH_2=CHRSiX_2/R_2SiX_2/R_3SiX$
$CH_2=CHSiR_3/R_3Si_2X_3$
$R_2SiX(CH_2X)/R_3Si_2X_3$
$X_2RSiCH_2CH_2X_2RSi/CH_2=CHSiR_3$

FUNCTIONALITY

A key feature of the present invention is the concept of the average molar functionality, F, of the compound system (i.e. single compound or mixture of compounds) from which the novel branched polycarbosilanes of the invention are made. Specific compounds useful according to the present invention can be assigned specific functionality values, f as listed below:

| Compound | Formula | f* |
|---|---|---|
| Trimethylchlorosilane | $Me_3SiCl$ | 1 |
| Dimethyldichlorosilane | $Me_2SiCl_2$ | 2 |
| Methyltrichlorosilane | $MeSiCl_3$ | 3 |
| Tetrachlorosilane | $SiCl_4$ | 4 |
| Chloromethyltrimethylsilane | $Me_3SiCH_2Cl$ | 1 |
| Bis(Chloromethyl)dimethylsilane | $Me_2Si(CH_2Cl)_2$ | 2 |
| Tris(chloromethyl)methylsilane | $MeSi(CH_2Cl)_3$ | 3 |
| Tetrakis(chloromethyl)silane+ | $Si(CH_2Cl)_4$ | 4 |
| Chloromethyldimethylchlorosilane | $ClCH_2SiMe_2Cl$ | 2 |
| Bis(chloromethyl)dichlorosilane | $(ClCH_2)_2SiMeCl$ | 3 |
| Tris(chloromethyl)chlorosilane | $(ClCH_2)_3SiCl$ | 4 |
| Chloromethylmethyldichlorosilane | $ClCH_2SiMeCl_2$ | 3 |
| Bis(Chloromethyl)dichlorosilane | $(ClCH_2)_2SiCl_2$ | 4 |
| Chloromethyltrichlorosilane | $ClCH_2SiCl_3$ | 4 |
| Vinyltrichlorosilane | $CH_2=CHSiCl_3$ | 5 |
| Vinylmethyldichlorosilane | $CH_2=CHSiMeCl_2$ | 4 |
| Vinyldimethylchlorosilane | $CH_2=CHSiMe_2Cl$ | 3 |
| Vinyltrimethylsilane | $CH_2=CHSiMe_3$ | 2 |
| Vinyldimethylchloromethylsilane | $CH_2=CHSiMe_2CH_2Cl$ | 3 |
| Bis(chloromethyl)vinyl-methylsilane+ | $CH_2=CHSiMe(CH_2Cl)_2$ | 4 |
| Vinyltris(chloromethyl)silane+ | $CH_2=CHSi(CH_2Cl)_3$ | 5 |
| Bis(chloromethyl)vinyl-chlorosilane+ | $CH_2=CHSiCl(CH_2Cl)_2$ | 5 |
| Chloromethylvinyldichlorosilane | $CH_2=CHSiCl_2CH_2Cl$ | 5 |
| Chloromethylvinylmethyl-chlorosilane | $CH_2=CHSiMeClCH_2Cl$ | 4 |
| 1,1-Dichlorotetramethyldisilane | $Cl_2MeSiSiMe_3$ | 2 |
| 1,2-Dichlorotetramethyldisilane | $ClMe_2SiSiMe_2Cl$ | 2 |
| 1,1,2-Trichlorotrimethyldisilane | $Cl_2MeSiSiMe_2Cl$ | 3 |
| 1,1,2,2-Tetrachlorodimethyldisilane | $Cl_2MeSiSiMeCl_2$ | 4 |
| 1,2-Bis(chlorodimethylsilyl)ethane | $ClMe_2Si(CH_2)_2SiMe_2Cl$ | 2 |
| 2-(Chlorodimethylsilyl)ethyl-methyldichlorosilane | $ClMe_2Si(CH_2)_2SiMeCl_2$ | 3 |
| 1,2-Bis(dichloromethylsilyl)ethane | $Cl_2MeSi(CH_2)_2SiMeCl_2$ | 4 |

*Note that vinylic silanes can add additional units of functionality in higher temperature reactions (see discussion infra).
+These compounds are conceptually useful in the present invention; however, they have not been reported in the prior art.

These f values represent the number of bonds which each compound can form with other molecules, including formation of both SiC and SiSi bonds, and can be used to calculate average molar functionality values, F, for polycarbosilanes prepared from known mixtures of silane monomers. The chemistry of bond formation is straightforward, involving active metal dechlorination (1) or disilylation (2) of the vinyl groups.

$$2\ SiCl + 2K \longrightarrow SiSi + 2KCl \quad (1)$$

$$SiCl + CCl + 2K \longrightarrow SiC + 2KCl$$

$$2\ SiCl + CH_2=CHSi + 2K \longrightarrow SiCH_2CH(Si)_2 + 2KCl \quad (2)$$

When the vinylic organosilane contains no silicon-bonded chlorine, reactions are observed at the vinyl group. Dunogues et al., Compt. Rend., 278C, 467–70

(1974), have shown that at high temperatures the vinyl group can be polyfunctional

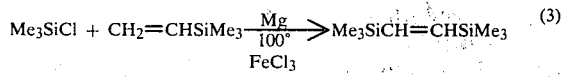

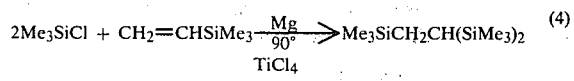

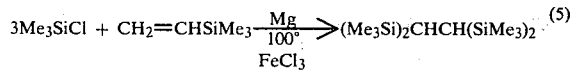

The molar functionality, F, of a polycarbosilane is identical to that of the compound system from which it is prepared. For a polycarbosilane prepared from a single monomer, F is equal to f. For a polycarbosilane prepared from a mixture, the molar functionality F is dependent upon the molar ratios of the monomers as well as their f values. For example, F for a polycarbosilane prepared from a mixture of monomers having respective functionality values $f_1$, $f_2$, and $f_3$, in the molar ratio x/y/z, can be calculated from the equation:

$$F = \frac{xf_1 + yf_2 + zf_3}{(x + y + z)}$$

Preferred molar functionality values for ractable solid polycarbosilanes are greater than two (F>2) requiring that at least one of the compounds has an f value of 3 or higher, i.e., that the polycarbosilane is branched, rather than linear.

A second proviso is that a plurality of the silyl units in the polycarbosilane must be branching sites in the polymer backbone. A third proviso is that compound systems must be selected such that the major polymerization reaction is formation of silicon-carbon bonds.

The property which the polycarbosilanes of the present invention possess, namely their ability to be converted into silicon carbide compositions by ambient pressure pyrolysis, is believed to be due to their branched structures. The degree of branching and the molecular weight can be controlled, by appropriate choices of starting monomer systems and the molar ratios within such monomer systems, such that the products range from soluble oils to the preferred soluble solids to insoluble, infusable solids. Since the branching structures of certain of the polycarbosilanes of the present invention derive from the inherent functionalities of the monomers used, the yield of silicon carbide derived from such polycarbosilanes increases with the relative content of branched units.

PROCESSING

In the present invention, a compound system is reacted with an active metal in an inert solvent at an elevated temperature to generate novel branched polycarbosilanes.

The preferred active metal is potassium for reasons of high reactivity and low melting point. Lithium, sodium, and magnesium are less reactive; but they may be used if longer reaction times are acceptable. Alloys such as potassium/sodium may also be used.

The preferred solvent is anhydrous tetrahydrofuran. However, higher boiling solvents such as dioxane, 1,2-dimethoxyethane, and the like, or hydrocarbons such as octane, and the like, can be used, particularly with the less reactive metals. Hexamethylphosphoramide may also be used, but it is more costly and is a suspected carcinogen.

The combination of potassium as the active metal and tetrahydrofuran as the solvent allows reactions to occur at the reflux temperature of tetrahydrofuran, which is just above the melting point of potassium. This combination does not allow significant reaction of chlorosilyl groups with the tetrahydrofuran solvent; such reactions have been observed with sodium and magnesium.

The polycarbosilane-forming reactions of the present invention can be run in standard laboratory glassware or commercial equipment, under inert atmospheres at atmospheric pressures, with provisions for external heating and cooling, stirring, and for incremental addition of mixtures of monomers. Thus, the process of the present invention regarding polycarbosilane preparation is not narrowly critical with regard to equipment and requires no extraordinary equipment.

In a typical preparation, a weighed amount of potassium metal is placed in anhydrous tetrahydrofuran under an inert atmosphere. Heat is applied to reflux, melting the potassium, and addition of the compound system is begun, with stirring. The reactions are sufficiently exothermic at controlled addition rates to maintain reflux without application of external heat. After completion of addition, heat may be reapplied for any specified time period. Illustrative examples are supplied below.

Reaction conditions are thus not narrowly critical except that reaction temperature should, if possible, be maintained above the melting point of the active metal and stirring should be maintained to prevent caking of by-products salts. A slight excess of the active metal is desired to insure consumption of a majority of chlorosilyl groups. Reactions can be terminated by addition of a alkylating agent, such as methyl chloride, or a protic material, such as water and can be neutralized with acids such as HCl. Salt by-products are removed by filtration or by water washing and the insoluble polycarbosilanes, if any, collected by dissolving the filtered salt in water and filtering or filtering the organic layer remaining after water washing. The resultant polycarbosilane solution can be added to a non-solvent medium such as methanol/acetone, precipitating the tractable solid polycarbosilane fraction, which is collected and dried. The non-solvent mixture can be stripped to recover a liquid polycarbosilane residue, or the original polycarbosilane solution can be stripped to dryness yielding unfractionated soluble solid polycarbosilane. These reaction procedures are familiar to those skilled in the art and are typical of numerous active metal reactions.

SILICON CARBIDE

The novel branched polycarbosilanes of the present invention, ranging from soluble oils to insoluble solids, can be converted to silicon carbide compositions by themselves or in mixture with other components as disclosed for prior art polycarbosilanes, simply by heating in an inert atmosphere over specified time periods up to 1200° C. or beyond.

Most useful of the branched polycarbosilanes of the present invention are those which are, at room temperature, normally solid and soluble in non-protic organic solvents. They can be thermo-formed into a variety of shapes such as pellets, fibers, films, etc., or can be dissolved in a variety of solvents including carbon tetrachloride, methylene dichloride, trichloromethane, toluene, tetrahydrofuran, dioxane, and the like, to be cast from solution as films or spun from solution as fibers.

The range of polycarbosilanes can be used as binders for the shaping of infusible, insoluble powders such as silicon carbide or silicon nitride in the same fashion as prior art polycarbosilanes. Both shaped polycarbosilane articles and shaped polycarbosilane-bound articles can be converted to silicon carbide compositions by atmospheric pressure pyrolysis.

The shaping, spinning, and casting of the polycarbosilanes of the present invention can be performed in commercially available equipment designed for such purposes and known to those skilled in the art. Similarly, the pyrolyses are also performed in commercially available equipment designed for such work and also known to those skilled in the art. Sintering aids typical of such high temperature reactions may be employed if desired.

EXAMPLES

The following examples serve to demonstrate the improved processes and new compositions of the present invention. Examples A–F are not within the scope of the present claims. Examples 1–20 are illustrative, but are not intended to be limiting, regarding the claims of this invention.

All reactions were run in standard laboratory glassware of various sizes using heating mantles, mechanical stirrers with glass or stainless steel blades, thermometers, wet ice condensers, and provisions for maintentance of argon atmospheres. Temperatures are reported in Centigrade degrees, and the abbreviations Me, g, mm, ml, min, hr, and THF represent methyl, gram, millimeter, milliliter, minute, hour, and tetrahydrofuran, respectively. Reported yields are based on theoretical yields calculated from the silane mixture charged.

Laboratory pyrolyses were run in quartz reactors in a tube furnace up to 800° C., and in alumina reactors in a second tube furnace from 800° C. to 1200° C. No attempt was made to maximize yields by varying pyrolysis conditions.

EXAMPLE A: F=2.0

Reaction of 2/1 $Me_3SiCl/CH_2=CHSiMeCl_2$ With K in THF

In a 500 ml three-necked round bottom flask with standard taper fittings were combined 16.8 g (0.43 mol) of K metal chunks and 131.4 g anhydrous THF. The flask was fitted with heating mantle, mechanical stirrer with glass blade, thermometer, addition funnel, and wet ice condenser plus valves for maintaining an Ar atmosphere. Flask contents were heated to reflux (66°) melting the K and addition of a mixture of 23.3 g (0.215 mol) of $Me_3SiCl$ and 15.2 g (0.107 mol) of $CH_2=CHSiMeCl_2$ was begun. Addition was completed in 50 min, maintaining the reaction temperature at 66°–67.5° C. with no external heating. Heat was applied to maintain reflux for an additional 75 min. Reaction was terminated by dropwise addition of a solution of 5 g $H_2O$ in 15 ml THF. White solid precipitate was collected by suction filtration, rinsed with several small portions of THF, and dissolved in water. A clear solution was obtained with no insoluble polycarbosilane. The THF solution was vacuum stripped and distilled up to 25°/0.5 mm head temperature. There was obtained 16.7 g (71.9%) of non-distilled residue, a soluble polycarbosilane fluid (molar functionality F=2.0). The relatively high portion of the $Me_3SiCl$ endblocker (2:1) reduced and the molecular weight, preventing formation of soluble solid which characterizes the novel branched polycarbosilanes of the present invention.

Similar reactions using octane or toluene in place of THF gave respective yields of 46.4% or 42.4% of soluble polycarbosilane fluid. The reaction in toluene also yielded $\phi CH_2SiMe_3$ as a volatile product.

EXAMPLE B: F=2.0

Reaction of 1/1 $Me_3SiCl/CH_2=CHSiMe_2Cl$ With K in THF

In the apparatus of Example A were combined 18.6 g (0.48 mol) K metal and 136.0 g anhydrous THF. The system was heated to reflux, which was maintained over 50 min by the addition of a mixture of 26.0 g (0.24 mol) of $Me_3SiCl$ and 28.9 g (0.24 mol) of $CH_2=CHSiMe_2Cl$. Heat was applied to maintain reflux for another hr. Workup as in Example A left 16.0 g of polycarbosilane fluid (47.2%) which did not distill below 51°/0.05 mm (molar functionality F=2.0).

EXAMPLE C: F=1.33

Reaction of 2/1 $Me_3SiCl/CH_2=CHSiMe_3$ With K in THF

Reaction procedure of Examples A and B were followed with 17.3 g (0.44 mol) of K metal, 137.3 g anhydrous THF, and a mixture of 47.0 g (0.44 mol) of $Me_3SiCl$ and 44.0 g (0.44 mol) of $CH_2=CHSiMe_3$. Workup yielded 33.8 g $Me_3SiCH_2CH(SiMe_3)_2$, b.p. 38°/0.07 mm (62.4%), confirming that disilylation is the major reaction of vinyl groups in these polycarbosilane-forming reactions.

EXAMPLE D: F=2.0

Reaction of 1/1 $Me_2SiCl_2/CH_2=CHSiMe_3$ With K in THF

The procedure of Example A was repeated using 33.6 g (0.88 mol) of K metal, 187.7 g anhydrous THF and a mixture of 52.9 g (0.41 mol) of $Me_2SiCl_2$ and 41.0 g (0.41 mol) of $CH_2=CHSiMe_3$. Workup yielded 39.7 g (57.6%) of linear polycarbosilane fluid, b.p. greater than 99°/0.04 mm, having the average stru ure $[CH_2CH(SiMe_3)SiMe_2]_x$. Pyrolysis of this fluid to only 590° under an inert atmosphere at atmospheric pressure left less than 0.3% residue. This example confirms that the linear polycarbosilane disclosed by Nefedov et al., *Proc.Acad.Sci., USSR*, 154, 76-8, (1964), is not an effective precursor for silicon carbide when pyrolyzed at atmospheric pressure under an inert atmosphere.

EXAMPLE E: F=2.0

Reaction of $ClCH_2SiMe_2Cl$ With K in THF

The procedure of Example A was repeated using 16.7 g (0.42 mol) of K metal, 30.0 g (0.21 mol) of $ClCH_2SiMe_2Cl$, and 194.5 g anhydrous THF. Workup yielded 10.6 (79.2%) of polysilmethylene fluid, b.p. greater than 70°/0.1 mm. Pyrolysis to only 585° C. left less than 1% residue confirming that linear polycarbosilanes such as polysilmethylenes known from Goodwin, U.S. Pat. No. 2,483,972 and Knoth, U.S. Pat. No. 2,850,514, are not effective precursors for silicon carbide when pyrolyzed at atmospheric pressure under an inert atmosphere.

EXAMPLE F: F=2.1

Reaction of 19.25/1 Me$_2$SiCl$_2$/CH$_2$=CHSiMeCl$_2$ With K in THF

The procedure of Example A was repeated using 33.3 g (0.85 mol) of K metal, 248 g anhydrous THF and a mixture of 49.7 g (0.385 mol) of Me$_2$SiCl$_2$ and 2.8 g (0.02 mol) of CH$_2$=CHSiMeCl$_2$. Additional THF (45 ml) was added after the exothermic addition was completed to reduce viscosity. Workup yielded 11.5 g of solid which was insoluble in THF (48.5%) and 12.0 g (50.6%) of solid which was soluble in THF. The THF-soluble solid was shown to be mainly cycli-hexamer, (Me$_2$Si)$_6$, by gas chromatography. The THF-insoluble solid was pyrolyzed at atmospheric pressure to only 675°, leaving only 2.6% residue, confirming that the reaction product of 19.25/1Me$_2$SiCl$_2$/CH$_2$=CHSiMeCl$_2$ as disclosed in Example 11, Japanese Kokai Tokkyo Koho 1979-65,799, is not an effective precursor for silicon carbide. Example 11 in fact discloses that simple distillation at 0.4 mm at 195° leaves only 15% residue, and 195° is well below temperatures needed for conversion to silicon carbide.

EXAMPLE 1: F=2.4

Reaction of 2/3 MeSiCl$_3$/ClCH$_2$SiMe$_2$Cl With K in THF

The procedures of Example E were repeated using 32.3 g (0.83 mol) of K metal, 326 g anhydrous THF, and a mixture of 19.6 g (0.13 mol) of MeSiCl$_3$ and 28.1 g (0.2 mol) of ClCH$_2$SiMe$_2$Cl. Workup yielded 7.8 g (39%) of soluble solid polycarbosilane. The solid was converted to an SiC composition (30.8% yield) by Pyrolysis in Ar to 1200° C. at atmospheric pressure. The presence of B-SiC was confirmed by x-ray diffraction. This example, with branching introduced by units derived from MeSiCl$_3$, confirms that branched structures are needed for conversion to SiC when results are compared to those of Example E.

EXAMPLE 2: F=2.57

Reaction of 3/1.2 ClCH$_2$SiMe$_2$Cl/CH$_2$=CHSiMeCl$_2$ With K in THF

The procedure of Example E was used with 50.0 g (1.28 mol) of K metal, 800 g of anhydrous THF, and a mixture of 57.9 g (0.405 mol) of ClCH$_2$SiMe$_2$Cl and 22.8 g (0.162 mol) of CH$_2$=CHSiMeCl$_2$. Workup yielded 17.7 g (43.7%) of soluble polycarbosilane fluid and 20.2 g (49.9%) of soft soluble solid polycarbosilane. The molar functionality F was 2.57. The solid was pyrolyzed to an SiC composition under Ar atmosphere at atmospheric pressure with a yield of 12.6%. This example demonstrates that polysilmethylenes which are branched due to incorporation of CH$_2$=CHSiMeCl$_2$-derived units do yield SiC on pyrolysis while linear polysilmethylenes (Example E) do not.

EXAMPLE 3: F=2.4

Reaction of 2/3 MeSiCl$_3$/CH$_2$=CHSiMe$_3$ With K in THF

The procedures of Example D were followed using 18.2 g (0.46 mol) of K metal, 180 g of anhydrous THF, and a mixture of 22.4 g (0.15 mol) of MeSiCl$_3$ and 23.0 g (0.23 mol) of CH$_2$=CHSiMe$_3$. Workup yielded 6.0 g (20%) of soluble solid polycarbosilane and 0.8 g (2.3%) of insoluble solid polycarbosilane. The molar functionality F was 2.4. The soluble solid was converted to an SiC composition (40.9% yield) by pyrolysis to 1200° C. under Ar atmosphere at atmospheric pressure. X-ray diffraction confirmed conversion to B-SiC. This example confirms that the branching introduced by MeSiCl$_3$ is needed for conversion to SiC when compared to the linear polycarbosilane of Example D.

EXAMPLE 4: F=2.67

Reaction of 0.8/1 Me$_2$SiCl/CH$_2$=CHSiMeCl$_2$ With K in THF

The procedure of Example A was repeated using a 1000 ml flask, 72.4 g (1.85 mol) K metal, 508.8 g anhydrous THF, and a mixture of 56.4 g (0.52 mol) of Me$_3$SiCl and 94.5 g (0.67 mol) of CH$_2$=CHSiMeCl$_2$. Similar workup yielded a yellow fluid which was added to 550 ml acetone, precipitating a white solid. The solid dissolved in a equal volume of CCl$_4$ and reprecipitated from 900 ml acetone, followed by filtration and vacuum drying. The organic phases wre stripped and distilled at 69°/0.08 mm, leaving a polycarbosilane fluid, while addition of the reaction salt a H O left insoluble polycarbosilane.

The yields were: soluble fluid, 37.1 g (43.7%), soluble solid, 21.4 g (25.2%), and insoluble solid, 14.0 g (16.5%). The molar functionality F was 2.67. The soluble and insoluble solids were converted to SiC compositions by heating to 1200° C. in an inert atmosphere at atmospheric pressure. B-SiC formation was confirmed by x-ray diffraction, with the yield of SiC composition being 43.6% for the soluble solid.

EXAMPLE 5: F=2.4

Reaction of 0.6/1/1 Me$_3$SiCl/Me$_2$SiCl$_2$/CH$_2$=CHSiMeCl$_2$ With K in THF The procedure of Example 4 was followed using a 500 ml flask with 35.0 g (0.9 mol) K metal, 166.0 g anhydrous THF, and a mixture of 12.6 g (0.12 mol) of Me$_3$SiCl, 25.3 g (0.2 mol) of Me$_2$SiCl$_2$, and 27.6 g (0.2 mol) of CH$_2$=CHSiMeCl$_2$. Workup yielded 38.1% (12.6 g) of polycarbosilane fluid (b.p. greater than 65°/0.06 mm) and 17.3 g (52.1%) of soluble solid polycarbosilane with no insoluble solid polycarbosilane. The molar functionality F was 2.54. The soluble solid was converted to an SiC composition (34.3% yield) by pyrolysis up to 1200° under Ar at atmospheric pressure, with B-SiC formation confirmed by x-ray diffraction. The polycarbosilane fluid was also converted to an SiC composition with a lower relative yield.

EXAMPLE 6: F=2.60

Reaction of 0.5/1/1 Me$_3$SiCl/Me$_2$SiCl$_2$/CH$_2$=CHSiMeCl$_2$ With K in THF The procedure of Example 5 was repeated with 33.2 g (0.85 mol) of K metal, 201.5 g anhydrous THF, and a mixture of 10.2 g (0.09 mol) of Me$_3$SiCl, 24.4 g (0.19 mol) of Me$_2$SiCl$_2$, and 26.6 g (0.19 mol) of CH$_2$=CHSiMeCl$_2$. Workup as in Example 5 yielded 9.8 g (31.2%) of soluble polycarbosilane fluid, 18.0 g (58.0%) of soluble solid polycarbosilane, and 2.7 g (8.7%) of insoluble solid polycarbosilane. Pyrolysis as in Example 5 of the soluble solid yielded 35.7% of an SiC composition. The molar functionality F was 2.60.

EXAMPLE 7: F=2.60

Reaction of 0.5/1/1 Me$_3$SiCl/Me$_2$SiCl$_2$/CH$_2$=CHSiMeCl$_2$ With K in THF The reaction of Example 6 was repeated with 336.3 g (9.6 mol) of K metal, 1463.0 g anhydrous THF, and a mixture of 100.9 g (0.93 mol) of Me$_3$SiCl, 239.9 g (1.86 mol) of Me$_2$SiCl$_2$, and 262.3 g (1.86 mol) of CH$_2$=CHSiMeCl$_2$. Reaction maintained itself at reflux throughout time of addition (3 hr), and was followed by heating at reflux for 2 hr. Workup yielded 52.7 g (17.2%) of soluble polycarbosilane fluid, b.p. greater than 55°/0.05 mm, 186.7 g (61.0%) of soluble solid polycarbosilane, and 59.7 g (19.5%) of insoluble solid polycarbosilane. Samples of the soluble fluid, the soluble solid, and the insoluble solid were pyrolyzed to 1200° C. under Ar at atmospheric pressure. Each was converted to an SiC composition, with the respective yields being 21.1%, 42.9%, and 41.5%. Formation of B-SiC was confirmed in each case by x-ray diffraction.

EXAMPLE 8: F=2.60

Reaction of 0.5/1/1 Me$_3$SiCl/Me$_2$SiCl$_2$/CH$_2$=CHSiMeCl$_2$ With Na in Toluene The reaction of Example 6 was repeated except that Na in toluene was used instead of K in THF. The reactants used were 21.0 g (0.9 mol) of Na, 175.0 g anhydrous toluene, and a mixture of 10.9 g (0.1 mol) of Me$_3$SiCl, 25.8 g (0.2 mol) of Me$_2$SiCl$_2$, and 28.2 g (0.2 mol) of CH$_2$=CHSiMeCl$_2$. Workup yielded 6.0 g (18 . . . 2%) of soluble polycarbosilane fluid, 0.4 g (1.2%) of soluble solid polycarbosilane, and 20.7 g (62.9%) of insoluble solid poycarbosilane. This example indicates that the higher reflux temperature of toluene relative to THF and the use of Na relative to K metal results in higher crosslink density and a lower yield of soluble solid. Pyrolysis of the insoluble solid to 1200° to yielded 43.9% of SiC composition. The presence of microcrystalline B-Si-C was confirmed by X-ray diffraction.

EXAMPLE 9: F=2.64

Reaction of 0.6/0.6/1 Me$_3$SiCl/Me$_2$SiCl$_2$/CH$_2$=CHSiMeCl$_2$ With K in THF The procedures of Example 6 were followed with 34.2 g (0.88 mol) of K metal, 167.1 g anhydrous THF, and a mixture of 15.2 g (0.14 mol) of Me$_3$SiCl, 18.1 g (0.14 mol) of Me$_2$SiCl$_2$, and 32.4 g (0.23 mol) of CH$_2$=CHSiMeCl$_2$. Workup yielded 11.0 g (31.9%) of soluble polycarbosilane fluid, 19.3 g (44.4%) of soluble solid polycarbosilane, and 3.2 g (9.3%) of insoluble solid polycarbosilane. The molar functionality F was 2.64. The soluble solid was pyrolyzed to an SiC composition with a yield of 42.9%.

EXAMPLE 10: F=2.52

Reaction of 0.5/1.4/1 Me$_3$SiCl/Me$_2$SiCl$_2$/CH$_2$=CHSiMeCl$_2$ With K in THF The procedures of Example 6 were repeated with 36.2 g (0.93 mol) of K metal, 200.6 g of anhydrous THF, and a mixture of 9.5 g (0.088 mol) of Me$_3$SiCl, 31.6 g (0.245 mol) of Me$_2$SiCl$_2$, and 24.7 g (0.175 mol) of CH$_2$=CHSiMeCl$_2$. Workup yielded 13.2 g (40.2%) of soluble polycarbosilane fluid and 18.0 g (56.0%) of soluble solid polycarbosilane with no insoluble solid polycarbosilane. Molar functionality F was 2.52. The soluble solid polycarbosilane was pyrolyzed to an SiC composition with no insoluble solid polycarbosilane. Molar functionality F was 2.52. The soluble solid polycarbosilane was pyrolyzed to an SiC composition with a yield of 27.1%.

EXAMPLE 11: F=2.6

Reaction of 0.5/1/1 Me$_3$SiCl/ClCH$_2$SiMe$_2$Cl/CH$_2$=CHSiMeCl$_2$ With K in THF The procedure of Example 6 was repeated using 32.6 g (0.83 mole) of K metal, 210.8 g of anhydrous THF, and a mixture of 9.6 g (0.09 mol) of Me$_3$SiCl, 25.2 g (0.18 mol) of ClCH$_2$SiMe$_2$Cl, and 24.8 g (0.18 mol) of CH$_2$=CHSiMeCl$_2$. Workup yielded 6.4 g soluble polycarbosilane fluid, b.p. greater than 50°/0.03 mm (20.4%), and 19.7 g (62.4%) of soluble solid polycarbosilane with no insoluble solid polycarbosilane. The soluble yielded 19.3% of an SiC composition on pyrolysis under Ar at atmospheric pressure.

EXAMPLE 12: F=2.67

Reaction of 1/1/1 Me$_3$SiCl/CH$_2$=CHSiMe$_2$Cl/CH$_2$=CHSiMeCl$_2$ With K in THF The procedures of Example 6 were repeated with 33.4 g (0.86 mol) of K metal, 192.0 g anhydrous THF, and a mixture of 22.1 g (0.205 mol) of Me$_3$SiCl, 24.6 g (0.205 mol) of CH$_2$=CHSiMe$_2$Cl, and 28.9 g (0.205 mol) of CH$_2$=CHSiMe$_2$Cl. Workup yielded 17.2 g (35.8%) of soluble polycarbosilane fluid, 16.2 g (34.7%) of soluble solid polycarbosilane, and 3.1 (6.6%) of insoluble solid polycarbosilane. The molar functionality F was 2.67. The soluble solid was pyrolyzed to an SiC composition under an inert atmospheric at atmospheric pressure was a yield of 24%.

EXAMPLE 13: F=2.72

Reaction of 0.9/1/1 Me$_3$SiCl/CH$_2$=CHSiMe$_2$Cl/CH$_2$=CHSiMeCl$_2$ With K in THF Example 12 was repeated with 35.2 g (0.9 mol) of K metal, 204.3 g anhydrous THF, and a mixture of 21.7 g (0.2 mol) of Me$_3$SiCl, 26.5 g (0.22 mol) of CH$_2$=CHSiMe$_2$Cl, and 31.0 g (0.22 mol) of CH$_2$=CHSiMeCl$_2$. Workup yielded 6.2 g (12.7%) of soluble polycarbosilane fluid, 30.0 g (61.6%) of soluble solid polycarbosilane, and 4.8 g (9.9%) of insoluble solid polycarbosilane. The molar functionality F was 2..72. The soluble solid polycarbosilane was pyrolyzed at atmospheric pressure under argon to a SiC composition with a yield of 18.4%.

EXAMPLE 14: F=2.67

Reaction of 2/1 ClCH$_2$SiMe$_2$Cl/CH$_2$=CHSiMeCl$_2$ With K in THF

Example 2 was repeated except that 974.6 g of THF, 50.3 g K metal (1.29 mol), 58.6 g (0.41 mol) of ClCH$_2$SiMe$_2$Cl, and 28.9 g (0.205 mol) of CH$_2$=CHSiMeCl$_2$ were used. Workup yielded 29.6 g of soluble fluid (67.6%) and 11.9 g (27.1%) of soluble solid. Pyrolysis of the soluble solid yielded 23.3% of SiC composition, with the higher yield reflecting the higher content of branched structural units relative to Example 2.

EXAMPLE 15: F=3.0

Reaction of 1/1 ClCH₂SiMe₂Cl/CH₂=CHSiMeCl₂ With K in THF

Example 14 was repeated except that 900 g of THF, 50.1 g (1.28 mol) of K metal, 43.6 g (0.305 mol) of ClCH₂SiMe₂Cl, and 43.0 g (0.305 mol) of CH₂=CHSiMeCl₂ were used. Workup yielded 4.8 g (11.1%) of soluble fluid, 26.7 g (61.7%) of soluble solid, and 10.4 g (24.0%) of insoluble solid. The molar functionality F was 3.0. The soluble solid was pyrolyzed at atmospheric pressure, yielding 36.0% of SiC composition. The higher yield reflects the higher content of branched structural units when results are compared to those of Example 2 and Example 14.

EXAMPLE 16: F=2.4

Reaction of 2/3 Mixed Disilanes/CH₂=CHSiMe₃ With K in THF

The procedure of Example D was followed using 24.6 g (0.64 mol) of K metal, 331.7 g anhydrous THF, and a mixture of 41.7 g (0.20 mol as Me₃Si₂Cl₃) of mixed disilanes (from the direct reaction of methyl chloride with silicon metal) and 30.0 g (0.3 mol) of CH₂=CHSiMe₃. Workup yielded 25.4 g (55.7%) of soluble solid polycarbosilane. Pyrolysis to 1200° yielded 27.3% of SiC composition, confirming that the incorporation of branched silyl units derived from Me₃Si₂Cl₃ is necessary when results are compared with Example D.

EXAMPLE 17: F=2.4

Reaction of 2/3 Mixed Disilanes/ClCH₂SiMe₂Cl With K in THF

The procedure of Example 16 was followed using 23.2 (0.59 mol) of K metal, 237.2 g anhydrous THF, and a mixture of 19.5 g (0.09 mol as Me₃Si₂Cl₃) of mixed disilanes and 20.2 g (0.14 mol) of ClCH₂SiMe₂Cl. Workup yielded 18.4 g (93.2%) of soluble solid polycarbosilane. Pyrolysis to 1200° yielded 14.7% of SiC composition, confirming that branching units derived from Me₃Si₂Cl₃ are needed for conversion to SiC when results are compared to Example E.

EXAMPLE 18: F=2.53

Reaction of 0.85/0.3/1.0 Me₃SiCl/Me₂SiCl₂/CH₂=CHSiMeCl₂ With K in THF

The procedure of Example 4 was followed using 436.2 g (11.2 mols) of K metal, 2098.3 g anhydrous THF, and a mixture of 284.1 g (2.62 mols) of Me₃SiCl, 119.2 g (0.92 mol) of Me₂SiCl₂, and 434.3 g (3.08 mol) of CH₂=CHSiMeCl₂. A 5 liter flask with a bottom take-off valve was employed. After termination with H₂O/THF and neutralization with conc. HCl, salts were removed as an aqueous lower layer by water washing with approximately 2 liters H₂O. The organic layer was dried and vacuum stripped, yielding 414.7 g (90.0%) of unfractionated soluble solid polycarboxilane. Pyrolysis of a small sample to 1200° yielded 32.1% of SiC composition.

EXAMPLE 19: Other Useful Silanes

Using procedures of preceding examples the silanes SiCl₄, Cl₂MeSiCH₂CH₂SiMeCl₂, ClCH₂SiMeCl₂, MeClSi(CH₂Cl)₂, and CH₃CH₂SiCl₃ have been used to provide branching sites in polycarbosilanes which were converted to SiC compositions. The silanes ClMe₂SiCH₂CH₂SiMe₂Cl and Me₂Si(CH₂Cl)₂ were coreacted with other silanes capable of providing branching sites to yield polycarbosilanes which were also convertible to SiC compositions by pyrolysis.

We claim:

1. A branched polycarbosilane comprising more than one unit of the formula

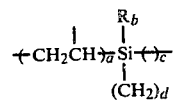

wherein R is lower alkyl, a is 0 or 1, b is 0–3, c is 0–4, d is 0–4, and a+b+c+d totals 4, with the provisos that, in different units, a, b, c, d, and R may differ, but that, in at least one unit, a+d must total 1 or more and, in at least 1 unit, a+c+d must total 3 or more.

2. The branched polycarbosilane of claim 1 wherein there are additionally units of the formula

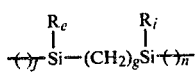

wherein R is lower alkyl, e, f, g, h and i are individually 0–3, and e+f+h+i totals 6 for each such unit with the proviso that in at least one such unit f+h totals 3 or more.

3. A branched polycarbosilane as in claim 1 substantially composed of, in the ratio shown, units of the formulas

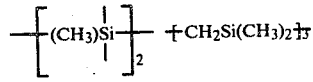

4. A branched polycarbosilane as in claim 1 substantially composed of units of the formulas

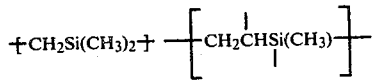

in a ratio selected from the group consisting of 3:1.2, 2:1, and 1:1.

5. A branched polycarbosilane as in claim 1 substantially composed of, in the ratio shown, units of the formulas

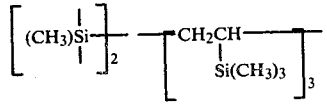

6. A branched polycarbosilane as in claim 1 substantially composed of, in the ratio shown, units of the formulas

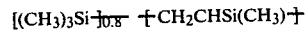

7. A branched polycarbosilane as in claim 1 substantially composed of units of the formulas

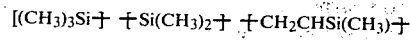

in a ratio selected from the group consisting of 0.6:1:1, 0.5:1:1, 0.6:6:1, 0.5:1.4:1, and 0.85:0.3:1.

8. A branched polycarbosilane as in claim 1 substantially composed of, in the ratio shown, units of the formulas

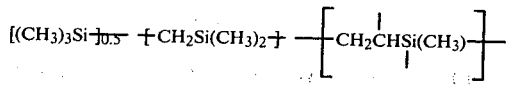

9. A branched polycarbosilane as in claim 1 substantially composed of units of the formulas

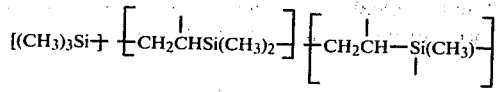

in a ratio selected from the group consisting of 1:1:1 and 0.9:1:1.

10. A branched polycarbosilane as in claim 2 substantially composed, in the ratio shown, of units of the formulas

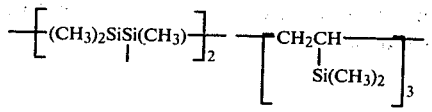

11. A branched polycarbosilane as in claim 2 substantially composed, in the ratio shown, of units of the formulas

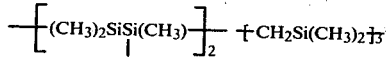

12. A branched polycarbosilane as in claim 1 wherein the branching derives from a member selected from the group consisting of $SiCl_4$, $ClCH_2Si(CH_3)Cl_2$, $Cl(CH_3)Si(CH_2Cl)_2$ and $CH_3CH_2SiCl_3$.

13. A branched polycarbosilane as in claim 2 wherein the branching derives from $Cl_2(CH_3)Si CH_2CH_2Si(CH_3)Cl_2$.

14. A process for producing branched polycarbosilanes which comprises reacting, with an active metal in an inert solvent at an elevated temperature, a compound system comprising one or more monomers of the formula (I)

$$(CH_2=CH)_a R_b SiX_c (CH_2X)_d \tag{I}$$

wherein R is lower alkyl, X is halo, a is 0 or 1, b is 0–3, c is 0–4, d is 0–4, a+b+c+d totals 4, and a+d totals at least 1, said compound system being selected such that its average molar functionality is at least 2.3, a plurality of silyl units are branching sites in the polymer backbone, and the formation of silicon-carbon bonds is favored.

15. The process of claim 14 wherein there is additionally units of the formula

wherein X is halo; R, e, f, g, h and i are individually of the same significance as set forth in claim 2 and e+f+h+i totals 6.

16. A process as in claim 14 wherein said monomer system contains at least two different monomers of formula (I), at least one of which is characterized by an a+c+d total of 3 or 4.

17. A process as in claim 16 wherein R is methyl and X is chloro.

18. A process as in claim 17 wherein the active metal is potassium, the solvent is tetrahydrofuran, and the elevated temperature is the ambient pressure reflux temperature of tetrahydrofuran.

19. The branched polycarbosilane product of the process of claim 14, 16, 17 or 18.

20. A branched polycarbosilane as claimed in claim 19 which, at room temperature, is normally solid and soluble in non-protic organic solvents.

* * * * *

UNITED STATES PATENT AND TRADEMARK OFFICE
CERTIFICATE OF CORRECTION

PATENT NO. : 4,414,403
DATED : November 8, 1983
INVENTOR(S) : Curtis L. Schilling, Jr., Thomas C. Williams and John P. Wesson It is certified that error appears in the above—identified patent and that said Letters Patent is hereby corrected as shown below:

Column 3, line 31, delete "r" and substitute therefor --R--.
Column 8, line 46, after "average" delete "stru ure" and substitute therefor --structure--.
Column 9, line 13, after "mainly" delete "cycli-hexamer" and substitute therefor --cyclic hexamer--.
Column 10, line 21, after "phases" delete "wre" and substitute therefor --were--.
Column 10, line 24, after "salt" delete "a H O left insoluble polycarbosilane" and substitute therefor --precipitate to $H_2O$ left insoluble polycarbosilane which was collected and vacuum dried--.
Column 11, line 32, after "6.0 g" delete "18...2%" and substitute therefor --18.2%--.
Column 11, line 39, after "1200°" delete "to".
Column 12, line 36, after "inert" delete the first occurence of "atmospheric" and substitute therefor --atmosphere--.
Column 12, line 51, after "was" delete "2..72" and substitute therefor --2.72--.
Column 14, claim 2, in the formula delete "n" and substitute therefor --h--.

Signed and Sealed this

Ninth Day of October 1984

[SEAL]

Attest:

GERALD J. MOSSINGHOFF

Attesting Officer

Commissioner of Patents and Trademarks